US010267913B2

(12) United States Patent
Smith et al.

(10) Patent No.: US 10,267,913 B2
(45) Date of Patent: *Apr. 23, 2019

(54) ALIGNMENT OF ULTRASOUND TRANSDUCER ARRAYS AND MULTIPLE APERTURE PROBE ASSEMBLY

(71) Applicant: MAUI IMAGING, INC., Sunnyvale, CA (US)

(72) Inventors: David M. Smith, Lodi, CA (US); Sharon L. Adam, San Jose, CA (US); Dennis R. Dietz, Littleton, CO (US)

(73) Assignee: MAUI IMAGING, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/364,092

(22) Filed: Nov. 29, 2016

(65) Prior Publication Data
US 2017/0074982 A1    Mar. 16, 2017

Related U.S. Application Data

(63) Continuation of application No. 14/210,015, filed on Mar. 13, 2014, now Pat. No. 9,510,806.
(Continued)

(51) Int. Cl.
    *G01S 15/89*    (2006.01)
    *G01S 7/52*     (2006.01)
    (Continued)

(52) U.S. Cl.
    CPC ........ *G01S 15/8927* (2013.01); *A61B 8/4461* (2013.01); *A61B 8/4477* (2013.01);
    (Continued)

(58) Field of Classification Search
    CPC ....... A61B 8/4461; A61B 8/4477; A61B 8/58; A61B 8/587; A61B 8/5207;
    (Continued)

(56) References Cited

U.S. PATENT DOCUMENTS

| 3,174,286 A | 3/1965 | Erickson |
|---|---|---|
| 3,895,381 A | 7/1975 | Kock |

(Continued)

FOREIGN PATENT DOCUMENTS

| CN | 1781460 A | 6/2006 |
|---|---|---|
| CN | 101116622 A | 2/2008 |

(Continued)

OTHER PUBLICATIONS

Belevich et al.; U.S. Appl. No. 15/400,826 entitled "Calibration of multiple aperture ultrasound probes," filed Jan. 6, 2017.
(Continued)

*Primary Examiner* — Daniel L Murphy
(74) *Attorney, Agent, or Firm* — Shay Glenn LLP

(57) ABSTRACT

The effective aperture of an ultrasound imaging probe can be increased by including more than one transducer array and using the transducer elements of all of the arrays to render an image can greatly improve the lateral resolution of the generated image. In order to render an image, the relative positions of all of the elements must be known precisely. Systems and methods for accurately calibrating and adjusting a multi-aperture ultrasound system are disclosed. The relative positions of the transducer elements can be computed and aligned prior to and during probe assembly.

8 Claims, 13 Drawing Sheets

Related U.S. Application Data

(60) Provisional application No. 61/780,366, filed on Mar. 13, 2013.

(51) Int. Cl.
*A61B 8/00* (2006.01)
*A61B 8/08* (2006.01)

(52) U.S. Cl.
CPC ............ *A61B 8/58* (2013.01); *G01S 7/52079* (2013.01); *A61B 8/5207* (2013.01); *A61B 8/587* (2013.01); *Y10T 29/49005* (2015.01); *Y10T 29/5313* (2015.01)

(58) Field of Classification Search
CPC ............ G01S 15/8927; G01S 7/52079; Y10T 29/5313; Y10T 29/49005
USPC ................... 367/140; 29/594, 729; 356/138
See application file for complete search history.

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A * | 2/1991 | Sliwa, Jr. ................ H01L 23/52 148/DIG. 28 |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |

(56) References Cited

U.S. PATENT DOCUMENTS

| | | |
|---|---|---|
| 6,363,033 B1 | 3/2002 | Cole et al. |
| 6,370,480 B1 | 4/2002 | Gupta et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,277,383 B2 | 10/2012 | Specht |
| 8,279,705 B2 | 10/2012 | Choi et al. |
| 8,412,307 B2 | 4/2013 | Willis et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,532,951 B2 | 9/2013 | Roy et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 9,072,495 B2 | 7/2015 | Specht |
| 9,146,313 B2 | 9/2015 | Specht et al. |
| 9,192,355 B2 | 11/2015 | Specht et al. |
| 9,220,478 B2 | 12/2015 | Smith et al. |
| 9,247,926 B2 | 2/2016 | Smith et al. |
| 9,265,484 B2 | 2/2016 | Brewer et al. |
| 9,282,945 B2 | 3/2016 | Smith et al. |
| 9,339,256 B2 | 5/2016 | Specht et al. |
| 9,420,994 B2 | 8/2016 | Specht |
| 9,510,806 B2 | 12/2016 | Smith et al. |
| 9,526,475 B2 | 12/2016 | Specht et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |

(56) References Cited

U.S. PATENT DOCUMENTS

| | | |
|---|---|---|
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbana et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0268503 A1* | 10/2010 | Specht ............ A61B 8/00 702/104 |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |

(56) References Cited

U.S. PATENT DOCUMENTS

| | | |
|---|---|---|
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0095347 A1 | 4/2012 | Adam et al. |
| 2012/0101378 A1 | 4/2012 | Lee |
| 2012/0114210 A1 | 5/2012 | Kim et al. |
| 2012/0116226 A1 | 5/2012 | Specht |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0144166 A1 | 6/2013 | Specht et al. |
| 2013/0204136 A1 | 8/2013 | Duric et al. |
| 2013/0204137 A1 | 8/2013 | Roy et al. |
| 2013/0253325 A1 | 9/2013 | Call et al. |
| 2013/0258805 A1 | 10/2013 | Hansen et al. |
| 2013/0261463 A1 | 10/2013 | Chiang et al. |
| 2014/0043933 A1 | 2/2014 | Belevich et al. |
| 2014/0058266 A1 | 2/2014 | Call et al. |
| 2014/0073921 A1 | 3/2014 | Specht et al. |
| 2014/0086014 A1 | 3/2014 | Kobayashi |
| 2014/0243673 A1 | 8/2014 | Anand et al. |
| 2015/0045668 A1 | 2/2015 | Smith et al. |
| 2015/0080727 A1 | 3/2015 | Specht et al. |
| 2016/0095579 A1 | 4/2016 | Smith et al. |
| 2016/0135783 A1 | 5/2016 | Brewer et al. |
| 2016/0157833 A1 | 6/2016 | Smith et al. |
| 2016/0256134 A1 | 9/2016 | Specht et al. |
| 2016/0354059 A1 | 12/2016 | Specht |

FOREIGN PATENT DOCUMENTS

| | | |
|---|---|---|
| CN | 101190134 A | 6/2008 |
| CN | 102018533 A | 4/2011 |
| CN | 102123668 A | 7/2011 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 B1 | 10/2011 |
| EP | 2385391 A2 | 11/2011 |
| EP | 2294400 B1 | 2/2012 |
| EP | 2453256 A2 | 5/2012 |
| EP | 1840594 B1 | 6/2012 |
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | 54-44375 A | 4/1979 |
| JP | S55-103839 A | 8/1980 |
| JP | 57-31848 A | 2/1982 |
| JP | 58-223059 A | 12/1983 |
| JP | 59-101143 A | 6/1984 |
| JP | 59-174151 A | 10/1984 |
| JP | 60-13109 U | 1/1985 |
| JP | 60-68836 A | 4/1985 |
| JP | 2-501431 A | 5/1990 |
| JP | 03126443 A | 5/1991 |
| JP | 04017842 A | 1/1992 |
| JP | 4-67856 A | 3/1992 |
| JP | 05-042138 A | 2/1993 |
| JP | 6-125908 A | 5/1994 |
| JP | 7-051266 A | 2/1995 |
| JP | 7-204201 A | 8/1995 |
| JP | 08-252253 A | 10/1996 |
| JP | 9-103429 A | 4/1997 |
| JP | 9-201361 A | 8/1997 |
| JP | 2777197 B | 5/1998 |
| JP | 10-216128 A | 8/1998 |
| JP | 11-089833 A | 4/1999 |
| JP | 11-239578 A | 9/1999 |
| JP | 2001-507794 A | 6/2001 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 A | 8/2004 |
| JP | 2004-337457 A | 12/2004 |
| JP | 2004-351214 A | 12/2004 |
| JP | 2005-152187 A | 6/2005 |
| JP | 2005-523792 A | 8/2005 |
| JP | 2005-526539 A | 9/2005 |
| JP | 2006051356 A | 2/2006 |
| JP | 2006-61203 A | 3/2006 |
| JP | 2006-122657 A | 5/2006 |
| JP | 2006130313 A | 5/2006 |
| JP | 2007-325937 A | 12/2007 |
| JP | 2008-122209 A | 5/2008 |
| JP | 2008-513763 A | 5/2008 |
| JP | 2008132342 A | 6/2008 |
| JP | 2008522642 A | 7/2008 |
| JP | 2008-259541 A | 10/2008 |
| JP | 2008279274 A | 11/2008 |
| JP | 2010-5375 A | 1/2010 |
| JP | 2010124842 A | 6/2010 |
| JP | 2010526626 A | 8/2010 |
| KR | 100715132 B | 4/2007 |
| KR | 1020090103408 A | 10/2009 |
| WO | WO92/18054 A1 | 10/1992 |
| WO | WO98/00719 A2 | 1/1998 |
| WO | WO01/64109 A1 | 9/2001 |
| WO | WO2005/009245 A1 | 2/2005 |
| WO | WO2006/114735 A1 | 11/2006 |
| WO | WO2007/127147 A2 | 11/2007 |
| WO | WO2009/060182 A2 | 5/2009 |
| WO | WO2010/095094 A1 | 8/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |

(56) References Cited

FOREIGN PATENT DOCUMENTS

| WO | WO2013/116851 A1 | 8/2013 |
|---|---|---|
| WO | WO2013/116854 A1 | 8/2013 |
| WO | WO2013/116866 A1 | 8/2013 |
| WO | WO2013/128301 A2 | 9/2013 |

OTHER PUBLICATIONS

Davies et al.; U.S. Appl. No. 15/418,534 entitled "Ultrasound imaging with sparse array probes," filed Jan. 27, 2017.
Call et al.; U.S. Appl. No. 15/500,933 entitled "Network-based ultrasound imaging system," filed Feb. 1, 2017.
Abeysekera et al.; Alignment and calibration of dual ultrasound transducers using a wedge phantom; Ultrasound in Medicine and Biology; 37(2); pp. 271-279; Feb. 2011.
Arigovindan et al.; Full motion and flow field recovery from echo doppler data; IEEE Transactions on Medical Imaging; 26(1); pp. 31-45; Jan. 2007.
Capineri et al.; A doppler system for dynamic vector velocity maps; Ultrasound in Medicine & Biology; 28(2); pp. 237-248; Feb. 28, 2002.
Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.
Chen et al.; Maximum-likelihood source localization and unknown sensor location estimation for wideband signals in the near-field; IEEE Transactions on Signal Processing; 50(8); pp. 1843-1854; Aug. 2002.
Chen et al.; Source localization and tracking of a wideband source using a randomly distributed beamforming sensor array; International Journal of High Performance Computing Applications; 16(3); pp. 259-272; Fall 2002.
Cristianini et al.; An Introduction to Support Vector Machines; Cambridge University Press; pp. 93-111; Mar. 2000.
Dunmire et al.; A brief history of vector doppler; Medical Imaging 2001; International Society for Optics and Photonics; pp. 200-214; May 30, 2001.
Du et al.; User parameter free approaches to multistatic adaptive ultrasound imaging; 5th IEEE International Symposium; pp. 1287-1290, May 2008.
Feigenbaum, Harvey, M.D.; Echocardiography; Lippincott Williams & Wilkins; Philadelphia; 5th Ed.; pp. 482, 484; Feb. 1994.
Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP—95; Detroit, MI; vol. 3 IEEE; pp. 1904-1907; May 9-12, 1995.
Haykin, Simon; Neural Networks: A Comprehensive Foundation (2nd Ed.); Prentice Hall; pp. 156-187; Jul. 16, 1998.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.
Hendee et al.; Medical Imaging Physics; Wiley-Liss, Inc. 4th Edition; Chap. 19-22; pp. 303-353; (year of pub. sufficiently earlier than effective US filing date and any foreign priority date) © 2002.
Hsu et al.; Real-time freehand 3D ultrasound calibration; CUED/F-INFENG/TR 565; Department of Engineering, University of Cambridge, United Kingdom; 14 pages; Sep. 2006.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Kramb et al.,.; Considerations for using phased array ultrasonics in a fully automated inspection system. Review of Quantitative Nondestructive Evaluation, vol. 23, ed. D. O. Thompson and D. E. Chimenti, pp. 817-825, (year of publication is sufficiently earlier than the effective U.S. filing date and any foreign priority date) 2004.
Ledesma-Carbayo et al.; Spatio-temporal nonrigid registration for ultrasound cardiac motion estimation; IEEE Trans. on Medical Imaging; vol. 24; No. 9; Sep. 2005.
Leotta et al.; Quantitative three-dimensional echocardiography by rapid imaging . . . ; J American Society of Echocardiography; vol. 10; No. 8; pp. 830-839; Oct. 1997.
Li et al.; An efficient speckle tracking algorithm for ultrasonic imaging; 24; pp. 215-228; Oct. 1, 2002.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Saad et al.; Computer vision approach for ultrasound doppler angle estimation; Journal of Digital Imaging; 22(6); pp. 681-688; Dec. 1, 2009.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. on Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.

(56) References Cited

OTHER PUBLICATIONS

Specht, D.F.; Probabilistic neural networks; Pergamon Press; Neural Networks; vol. 3; pp. 109-118; Feb. 1990.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.
Urban et al; Implementation of vibro-acoustography on a clinical ultrasound system; IEEE Ultrasonics Symposium (IUS); pp. 326-329; Oct. 14, 2010.
Von Ramm et al.; High-speed ultrasound volumetric imaging—System. 2. Parallel processing and image display; IEEE Trans. Ultrason., Ferroelect., Freq. Contr.; vol. 38; pp. 109-115; Mar. 1991.
Wang et al.; Photoacoustic tomography of biological tissues with high cross-section resolution: reconstruction and experiment; Medical Physics; 29(12); pp. 2799-2805; Dec. 2002.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Wikipedia; Point cloud; 2 pages; retrieved Nov. 24, 2014 from the internet (https://en.wikipedia.org/w/index.php?title=Point_cloud&oldid=472583138).
Wikipedia; Curve fitting; 5 pages; retrieved from the internet (http:en.wikipedia.org/wiki/Curve_fitting) Dec. 19, 2010.
Wikipedia; Speed of sound; 17 pages; retrieved from the internet (http:en.wikipedia.org/wiki/Speed_of_sound) Feb. 15, 2011.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Zhang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.
Specht et al.; U.S. Appl. No. 15/364,075 entitled "Point source transmission and speed-of-sound correction using multi-aperture ultrasound imaging," filed Nov. 29, 2016.

* cited by examiner

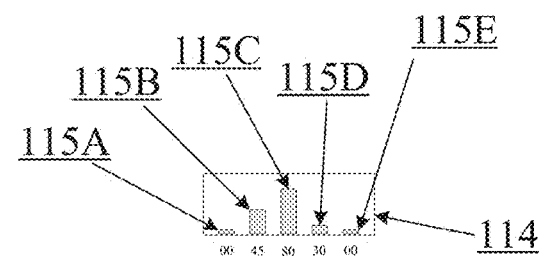
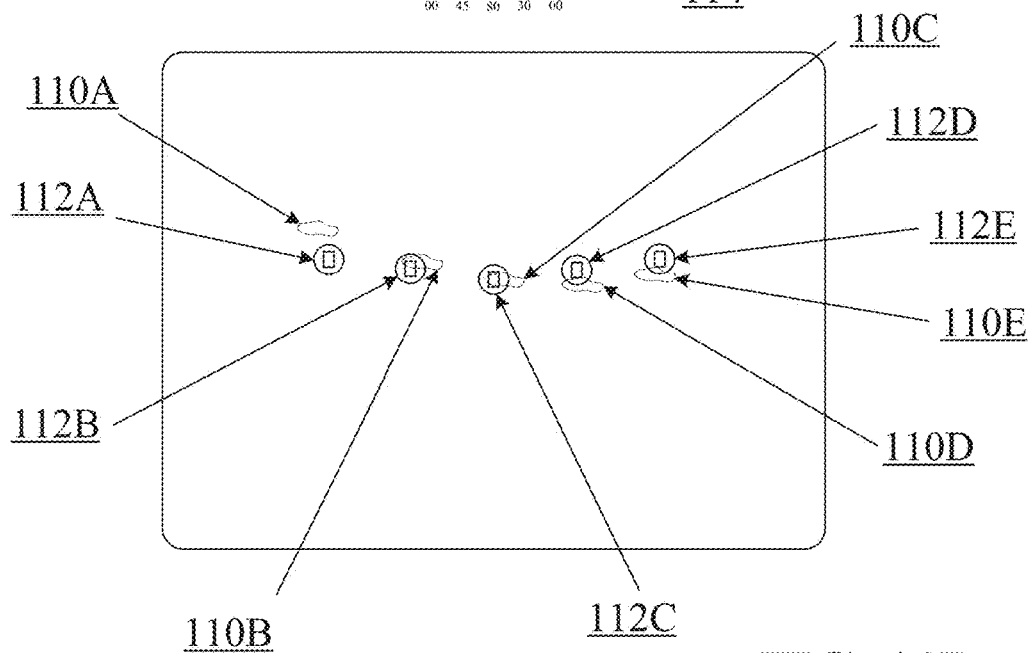
FIG. 11A
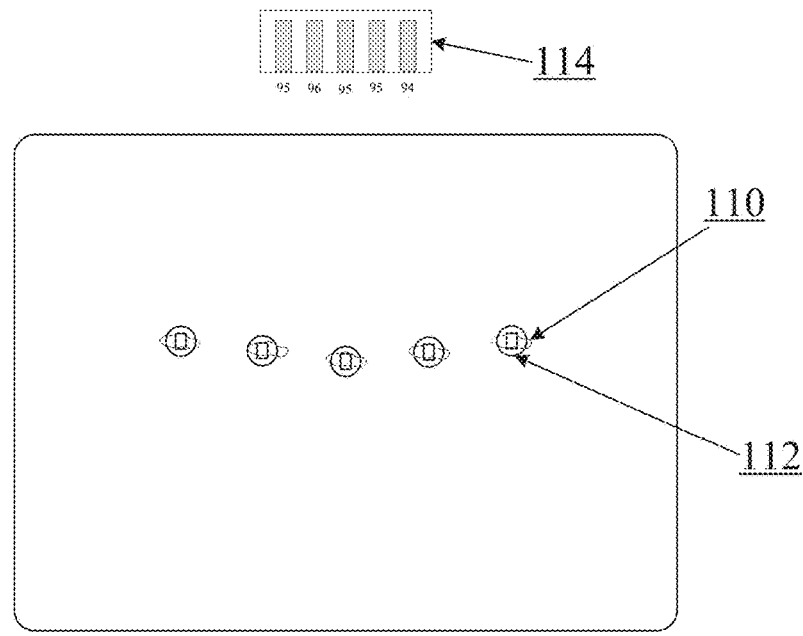
FIG. 11B

ALIGNMENT OF ULTRASOUND TRANSDUCER ARRAYS AND MULTIPLE APERTURE PROBE ASSEMBLY

CROSS-REFERENCE TO RELATED APPLICATIONS

This application is a continuation of U.S. application Ser. No. 14/210,015, filed Mar. 13, 2014, now U.S. Pat. No. 9,510,806, which application claims the benefit of U.S. Provisional Patent Application No. 61/780,366, filed Mar. 13, 2013, titled "Alignment of Ultrasound Transducer Arrays and Multiple Aperture Probe Assembly", the contents of each application incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to imaging techniques, and more particularly to ultrasound imaging, and still more particularly to systems and methods for calibration and quality assurance measurement of ultrasound probes, particularly probes having multiple apertures.

BACKGROUND

In conventional (scanline-based) ultrasonic imaging, a focused beam of ultrasound energy (a scanline) is transmitted into body tissues to be examined and echoes returning along the same scanline are detected and plotted. A complete image may be formed by combining multiple scanlines. While ultrasound has been used extensively for diagnostic purposes, conventional scanline-based ultrasound has been greatly limited by depth of scanning, speckle noise, poor lateral resolution, obscured tissues and other problems.

Significant improvements have been made in the field of ultrasound imaging with the creation of multiple aperture imaging, some examples of which are shown and described in U.S. Pat. No. 8,007,439 titled "Method and Apparatus to Produce Ultrasonic images Using Multiple Apertures," U.S. patent application Ser. No. 13/029,907, filed Feb. 18, 2010, now U.S. Pat. No. 9,146,313, titled "Point Source Transmission and Speed-Of-Sound Correction Using Multiple-Aperture Ultrasound Imaging, U.S. patent application Ser. No. 12/760,375, filed Apr. 4, 2010, titled "Universal Multiple Aperture Medical Ultrasound Probe," and U.S. patent application Ser. No. 12/760,327, now U.S. Pat. No. 8,473,239, titled "Multiple Aperture Ultrasound Array Alignment Fixture," all of which are incorporated herein by reference. Multiple aperture imaging methods and systems allow for ultrasound signals to be both transmitted and received from separate apertures.

Ultrasound probes constructed to perform multiple aperture ultrasound imaging typically contain multiple separate transducer arrays. During construction of such a probe, the multiple arrays need to be aligned in a common imaging plane and in a desired orientation relative to one another. Some methods of performing such alignment and construction are shown and described in U.S. patent application Ser. No. 12/760,327, now U.S. Pat. No. 8,473,239. Room for further improvement remains.

SUMMARY

In one embodiment, a method of building a multiple aperture ultrasound probe is provided, the method comprising the steps of forming a gasket with a first flowable solidifying material on a lower surface of a precision alignment element, securing the precision alignment element to a back surface of a transducer array with the gasket, evaluating and adjusting alignment of the transducer array relative to the precision alignment element, and injecting a second flowable solidifying material through at least one hole in the precision alignment element to secure the transducer array to the precision alignment element.

In some embodiments, the injecting step comprises filling a volume defined by the back surface of the transducer array, the lower surface of the precision alignment element, and an inner surface of the gasket with the second flowable solidifying material.

In some embodiments, the method further comprises allowing the second flowable solidifying material to solidify, and mounting the precision alignment element to a probe alignment bracket.

In alternative embodiments, the method further comprises placing the probe alignment bracket into a probe housing, and injecting a third flowable solidifying material into a space between the transducer array and the probe housing.

In other embodiments, the injected third flowable solidifying material surrounds at least a portion of the precision alignment element or the probe alignment bracket.

In one embodiment, evaluating alignment of the transducer array relative to the precision alignment element comprises imaging a target with the transducer array and comparing a resulting image of the target with known information defining a geometry of the target.

In some embodiments, the target comprises a plurality of pins oriented in a known configuration relative to the precision alignment element.

In other embodiments, each of the pins has a flat surface substantially perpendicular to a longitudinal axis of the pins, the longitudinal axis being substantially perpendicular to an ultrasound wavefront transmitted from a single element of the transducer array and arriving at the pins.

In some embodiments, adjusting alignment of the transducer array relative to the precision alignment element comprises adjusting at least one set screw to mechanically move the transducer array relative to the precision alignment element.

In some embodiments, the method further comprises allowing the first flowable solidifying material to solidify prior to evaluating and adjusting alignment of the transducer array relative to the precision alignment element.

In additional embodiments, the first flowable solidifying material and the second flowable solidifying material are the same material.

In one embodiment, the pins are oriented with longitudinal axes that intersect at a single point.

A method of evaluating an alignment of an ultrasound transducer array relative to a precision alignment element is also provided, the method comprising the steps of flexibly securing the ultrasound transducer array to the precision alignment element, mounting the precision alignment element in a fixed, known position and orientation relative to a target, the target having a plurality of reflectors in known reflector positions, imaging the reflectors of the target with the array, comparing imaged reflector positions with known reflector positions, and identifying a corrective adjustment based on the comparing step.

In some embodiments, the method further comprises comparing a brightness of the reflectors with expected brightness values.

In other embodiments, the method further comprises visually comparing imaged reflector positions with known reflector positions using a graphical user interface in which a first image comprising the imaged reflector positions is displayed simultaneously with a second image comprising the known reflector positions.

In alternative embodiments, the graphical user interface further comprises a graphical representation of a brightness of imaged reflectors within a predetermined radius of the known reflector positions.

An ultrasound probe alignment system is provided, comprising a tank assembly comprising an ultrasound conducting material, an array affixing and adjusting assembly at least partially within the tank assembly, the array affixing and adjusting assembly supporting a precision alignment element in a known position and orientation relative to a target assembly, the target assembly being disposed in the tank assembly and comprising at least one reflector configured to reflect an ultrasound signal.

Some embodiments further comprise a height adjustment assembly configured to adjust a distance between the array affixing and adjusting assembly and the target assembly.

In other embodiments, the target assembly comprises a plurality of pins arranged so as to be coincident with a precisely aligned imaging plane of the ultrasound probe alignment system.

In some embodiments, the pins are arranged so as to be displaced from one another in two dimensions in the imaging plane of the ultrasound probe alignment system.

In one embodiment, the pins vary in length so as to lie on multiple different points of the imaging plane of the ultrasound probe alignment system.

In alternative embodiments, the plurality of pins comprises a center pin and at least one pair of pins equidistant from the center pin.

In other embodiments, the array affixing and adjusting assembly comprises structures for adjusting an orientation of an ultrasound transducer array relative to the precision alignment element.

A multiple aperture ultrasound probe is provided, comprising a probe housing, a first transducer array secured to a first precision alignment element by a layer of a solidified polymer material, the first precision alignment element comprising a first plate secured to a back surface of the first transducer array, the first precision alignment element being secured to a probe bracket of the probe housing, a second transducer array secured to a second precision alignment element by a layer of a solidified polymer material, the second precision alignment element comprising a second plate secured to a back surface of the second transducer array, the second precision alignment element being secured to the probe bracket of the probe housing, and a filler solidified polymer material disposed in a space between the first and second transducer arrays and the probe housing.

In some embodiments, the first and second arrays are precisely aligned relative to the first and second precision alignment elements, respectively.

In other embodiments, the first precision alignment element comprises a plate having at least one hole through which a quantity of solidified polymer material extends.

In one embodiment, the plate comprises two holes, at least one of which has a quantity of solidified polymer material extending therethrough.

In some embodiments, the first precision alignment element is secured to a single surface of the first transducer array.

In additional embodiments, the first precision alignment element is secured to the probe bracket by a plurality of mechanical fasteners.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11A is an illustration of an embodiment of an array alignment display screen showing an image of an array that is out of alignment.

FIG. 11B is an illustration of an embodiment of an array alignment display screen showing an image of an array that is well-aligned.

DETAILED DESCRIPTION

Figure 1:
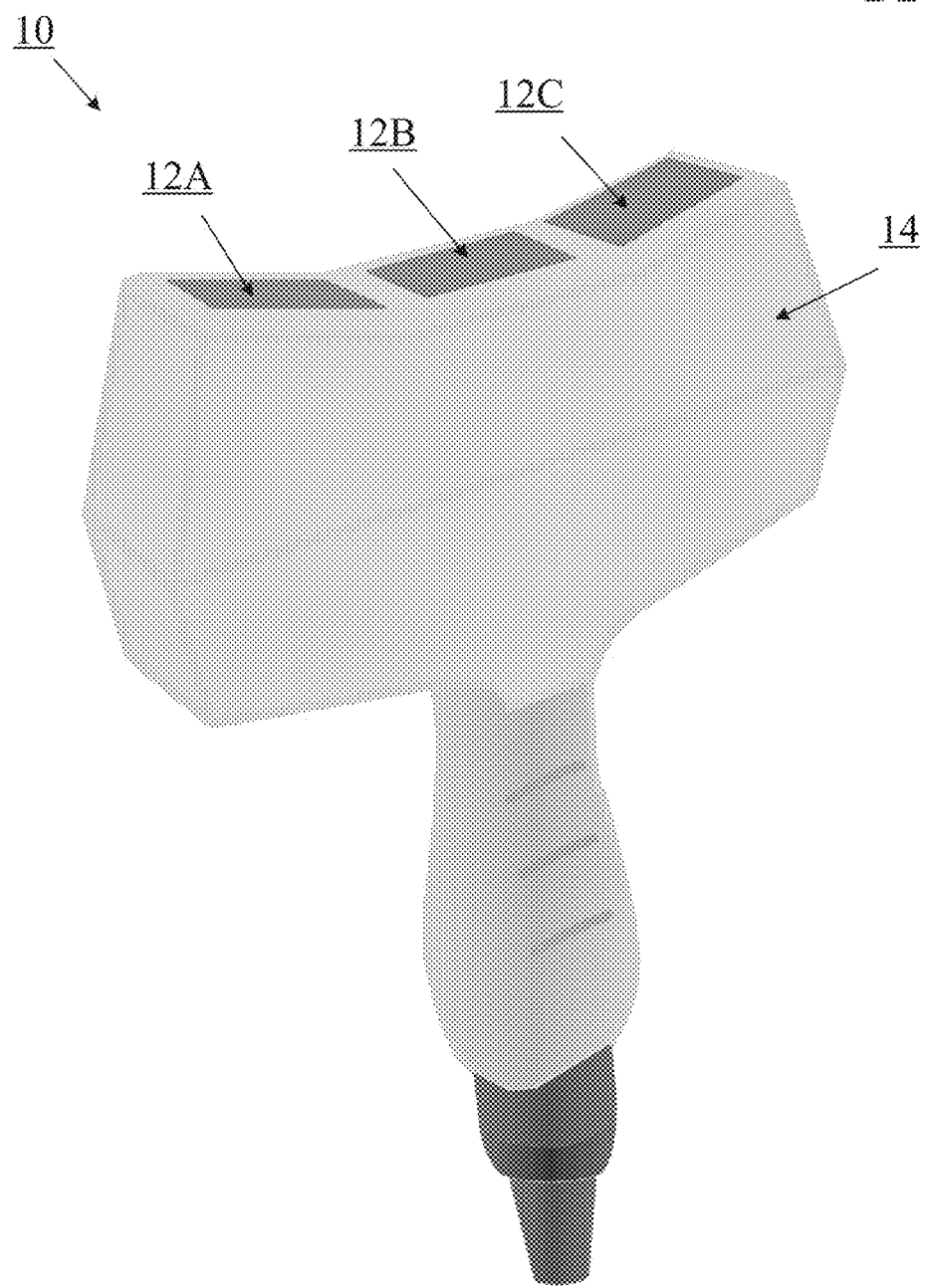
FIG. 1 is a perspective view of an embodiment of a fully assembled multiple aperture ultrasound imaging probe.

The following disclosure provides embodiments of systems and methods for constructing accurately aligned multiple aperture ultrasound probes. Some embodiments provide systems and methods for checking, adjusting, and securing the alignment of an individual array relative to a precision alignment element (PAE). Some embodiments provide systems and methods for mechanically aligning and affixing multiple transducer arrays in a desired alignment relative to one another and relative to a probe housing.

It is important that ultrasound probes to be used in high resolution multiple aperture ultrasound imaging be precisely constructed such that each of a plurality of transducer arrays be precisely aligned along a common imaging plane. It is further important that such arrays be mounted within a probe housing at a precise angle, orientation and position relative to each other and relative to the probe housing itself.

As used herein, references to the "exact" or "precise" position of transducer elements (and similar terms) may imply a relatively tight tolerance. For example, in some embodiments ultrasound probe calibration systems and methods may provide information describing the acoustic position of each transducer element in an array to within a distance of a fraction of a wavelength of ultrasound being used. In some embodiments, the acoustic position of transducer elements may be determined to within $\frac{1}{10}$ of a wavelength. In other embodiments, the acoustic position of transducer elements may be determined to within a tolerance of less than $\frac{1}{10}$ of a wavelength. In some embodiments, such as for calibrating a standard (i.e., single aperture) ultrasound probe, much looser tolerances may also be used, provided that such tolerances meet the needs of a particular system.

Conventional ultrasound (or "scanline based" ultrasound as used herein) utilizes a phased array controller to produce and steer a substantially linear transmit waveform groups. In order to produce a B-mode image, a sequence of such linear waveform groups (or "scanlines") may be produced and steered so as to scan across a region of interest. Echoes are received along each respective scanline in a process known as receive beamforming. The echoes received along the individual scanlines may then be combined to form a complete image.

In a ping-based imaging process, an unfocused circular wavefront is transmitted from a point source transmitter, and the echoes are received by a plurality of receive transducers. The received echoes may then be beamformed using a ping-based beamforming process in order to determine a display location for each reflector that returns an echo. Beamforming is generally understood to be a process by which imaging signals received at multiple discrete receptors are combined to form a complete coherent image. The process of ping-based beamforming is consistent with this understanding.

Embodiments of ping-based beamforming generally involve determining the position of reflectors corresponding to portions of received echo data based on the path along which an ultrasound signal may have traveled, an assumed-constant speed of sound and the elapsed time between a transmit ping and the time at which an echo is received. In other words, ping-based imaging involves a calculation of distance based on an assumed speed and a measured time. Once such a distance has been calculated, it is possible to triangulate the possible positions of any given reflector. This distance calculation is made possible with accurate information about the relative positions of transmit and receive transducer elements. Further details of ping-based imaging are described in U.S. patent application Ser. No. 13/029,907, now U.S. Pat. No. 9,146,313, referenced above.

Embodiments of Alignment Array Fixtures and Assemblies

FIG. 1 illustrates an assembled multiple aperture ultrasound probe 10. The probe 10 of FIG. 1 includes three separate transducer arrays 12A, 12B, 12C, each of which may be secured (or "potted") in a precise desired position and orientation within a probe housing 14. In some embodiments, the arrays may be potted in the probe housing 14 with a flowable solidifying material such as a room temperature vulcanizing (RTV) silicone rubber or any other similarly suitable epoxy or polymerizing material. RTV silicone is particularly suitable due to its thermal and mechanical properties, but other materials with similar properties may also be used. Generally any reference herein to a "flowable solidifying material," a "solidifying polymer material," a "flowable hardening material" or an "acoustic damping material" may refer to any suitable material that transitions from a liquid to a solid by a curing, drying or polymerizing process. Such materials may include RTV silicone, two-part epoxy resins, or others.

In general, it may be desirable for a flowable solidifying material to have properties in its solid state that are similar to properties of a medium to be imaged and similar to a lens material attached to a manufactured transducer array (which may also be specified for particular applications). RTV silicone is well-suited to medical applications while more rigid materials, such as hard-curing epoxies or a metal-impregnated epoxies may be well-suited to non-destructive testing applications. In still further embodiments, a flowable solidifying material may be a phase-changing material. For example, a molten plastic may be flowed as needed, and then allowed to solidify by cooling to a temperature below a melting point.

In various alternative embodiments, multiple aperture probes may be constructed with 2, 3, 4, 5, 6, 7, 8, 9, 10 or more individual transducer arrays in a common housing. In some embodiments, all transducer arrays in a probe may be oriented in a common imaging plane. In other embodiments, some arrays may be aligned in multiple imaging planes so as to facilitate 3D or 4D imaging. Generally, multiple aperture probes are designed with relatively tight tolerances for the position and orientation of arrays within the probe housing. In order to meet these tolerances while assembling a probe, an alignment and affixing process may be needed.

Figure 2:
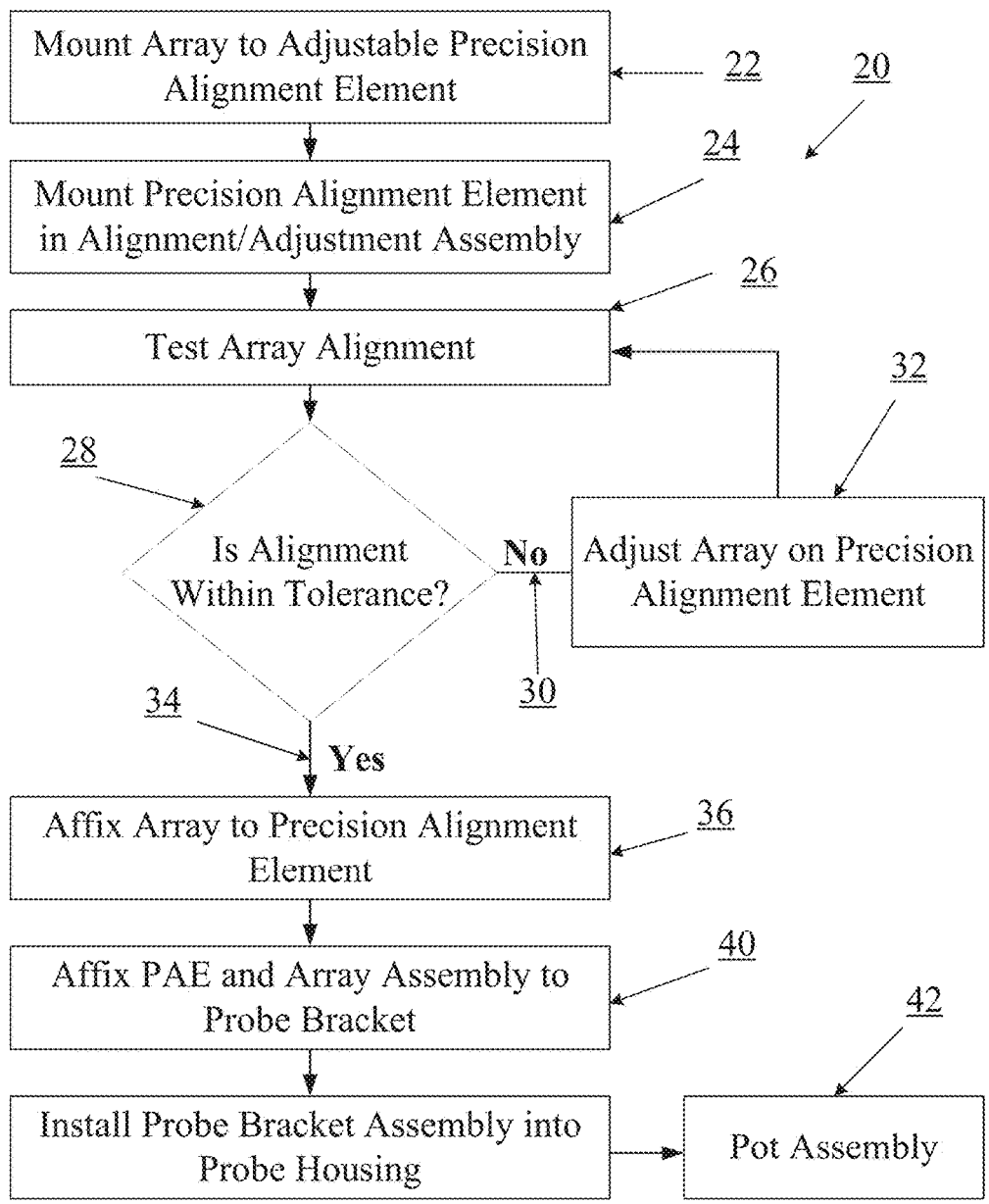
FIG. 2 is a flow chart illustrating an embodiment of a high-level process for aligning transducer arrays during assembly of a multiple aperture ultrasound probe.

FIG. 2 illustrates an example of a process 20 for aligning one or more arrays relative to a precision alignment element (PAE) and affixing the one or more arrays to the PAE. The process 20 of FIG. 2 may begin with the step of mounting an array to a PAE 22 in such a way as to allow for the position and/or orientation of the array to be adjusted relative to the PAE. The PAE may then be mounted 24 to an alignment/adjustment assembly. Using the alignment/adjustment assembly, the alignment of the array relative to the PAE may be tested 26. The result of the test may be evaluated 28 to determine whether the array is sufficiently aligned with the PAE. If the testing 26 reveals that the alignment of the array relative to the PAE is outside of a desired tolerance 30, then the array's alignment may be adjusted 32, and the alignment may be re-tested 26. Once the array is determined to be aligned with the PAE to within a desired degree of precision 34, the array may be more permanently affixed to the precision alignment assembly 36. The aligned array & PAE assembly may then be mounted to a probe alignment bracket 38, and when all such PAE/array assemblies are mounted to the probe bracket, the entire assembly may be placed into a probe housing 40, and the entire assembly may be permanently potted into the probe housing 42. The embodiments of various structures that may be used for such a process will now be described before describing further detailed embodiments of an alignment process 20.

Figure 3:
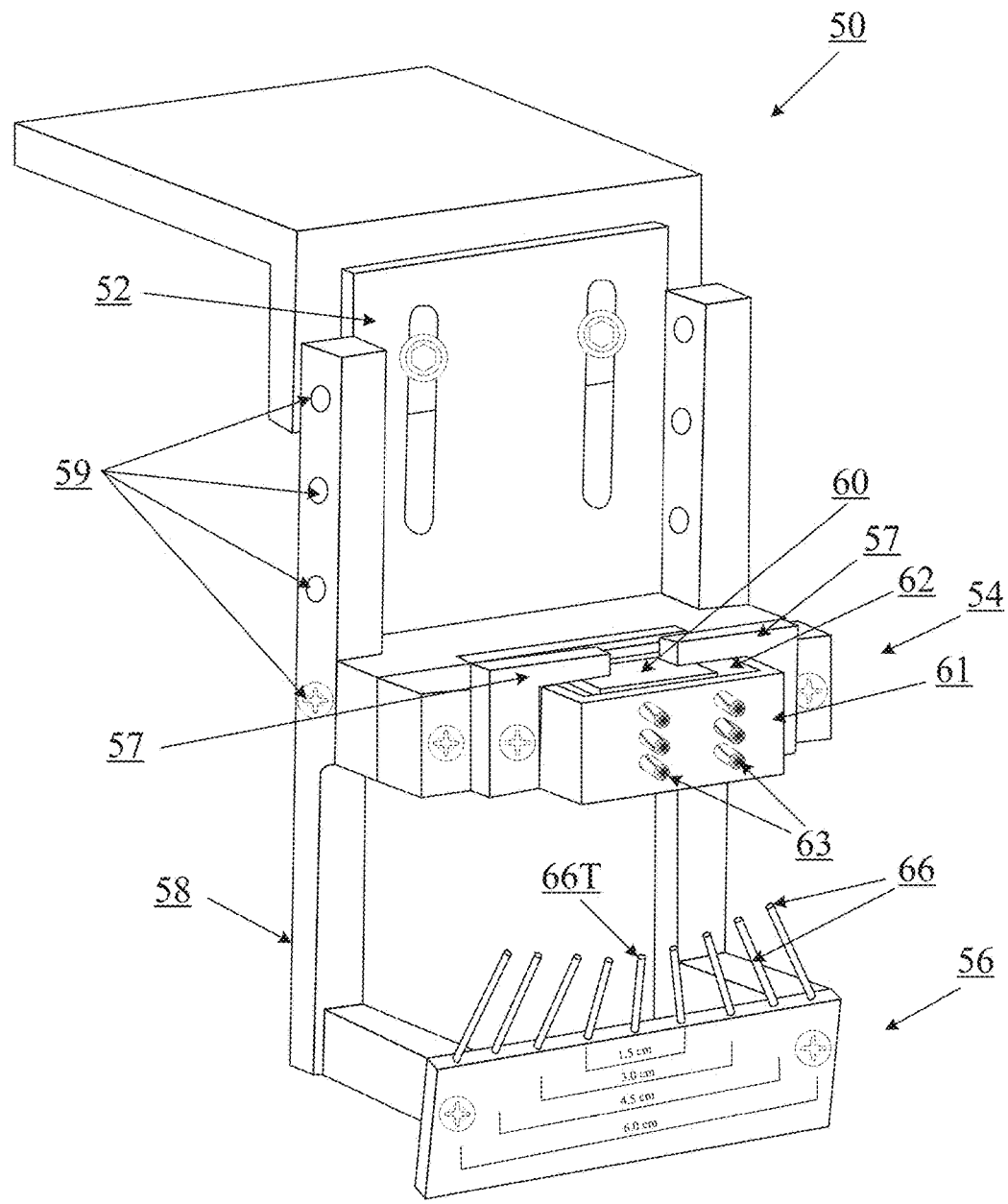
FIG. 3 is a perspective view of an embodiment of a fixture assembly and a target for aligning a transducer array.

FIG. 3 illustrates one embodiment of an alignment and adjustment assembly 50. In the illustrated embodiment, the assembly 50 may include a tank-affixing section 52, an array affixing and adjusting assembly 54, and a target assembly 56. The assembly 50 of FIG. 3 may be generally configured such that a PAE 60 may be supported in a known precisely aligned position and orientation relative to a target to be imaged, such as pins 66, 66T. The orientation of an array 62 attached to the PAE 60 may be tested by imaging the target 56 (or more particularly pins 66, 66T in some embodiments) using the array 62 and evaluating the resulting image (as described in further detail below). If the array 62 is found to be out of alignment, the orientation of the array 62 relative to the PAE 60 may be adjusted using the adjustment assembly 54 (as described in further detail below with reference to FIG. 9).

In the illustrated embodiment, the PAE 60 may be secured to the assembly 54 by arms 57. In alternative embodiments, any number of other structures may also be used depending on the shape and configuration of the PAE and other portions of the alignment assembly 50. In other embodiments, the PAE 60 may also include further structures and features designed to enable precise alignment of the PAE 60 with components of the assembly 54. An Adjustment cover 61 may also be provided to surround the array 62, and to provide structure for a plurality of adjustment screws 63.

In some such embodiments, the alignment assembly 50 of FIG. 3 may be configured to allow the distance between the array 62 and the target 56 to be increased or decreased by known amounts. For example, the array affixing and adjusting assembly 54 may be mountable at a plurality of discrete locations 59 relative to the target assembly 56. In alternative embodiments, a continuously variable height adjustment mechanism, such as a rack and pinion (or any other suitable mechanism) may be used to vary the height of the probe affixing assembly 54 relative to the target 56.

In some embodiments, all or part of the assembly 50 may be mounted relative to a tank containing a liquid bath such that at least the target assembly 56 and the emitting surface of the transducer array 62 may be submerged in a liquid medium with a known consistent speed of sound (e.g., water, gel, oil or other material as described in further detail below). In various embodiments, the tank-affixing section 52 may include any structure for affixing the assembly 50 relative to a water tank such that at least the array transducers 60 and the target 56 are submerged.

In other embodiments, the water tank may be omitted. For example, a target assembly 56 may be encased within a solid material with a known consistent speed-of-sound (e.g., RTV silicone, ballistic gelatin, or any other solid elastic material suitable for use in ultrasound phantoms), and the transducer array 60 to be aligned may be acoustically coupled to a surface of the target assembly by an acoustic coupling gel or a conformable bladder containing a liquid or gel. In such embodiments, the material in which the target is encased may be selected based on the frequency and style of array under test. For example, whereas medical transducers are designed in the 1 to 18 MHz area, ideal target-encasing materials may have similar characteristics to human tissue. On the other hand, a transducer to be used in non-destructive testing (NDT) of industrial materials may be designed to operate at substantially higher frequencies in order to evaluate metals and composites. Some NDT arrays may also be air-coupled, doing its job without ever touching the work surface. Such devices typically work at much lower frequencies. A coupling medium is a bridge to allow energy of an appropriate frequency to travel back and forth from the testing array to the object under test (e.g., a phantom containing an alignment target). In the case of medical arrays and some low frequency NDT arrays, a coupling medium may include compatible gels, lotions, oils or water depending on the materials to be imaged. Higher frequency NDT arrays might use water, oil or a combination of liquids as a coupling medium. In some embodiments, a coupling medium may comprise a flexible bladder or pad of a material with suitable properties.

Figure 4:
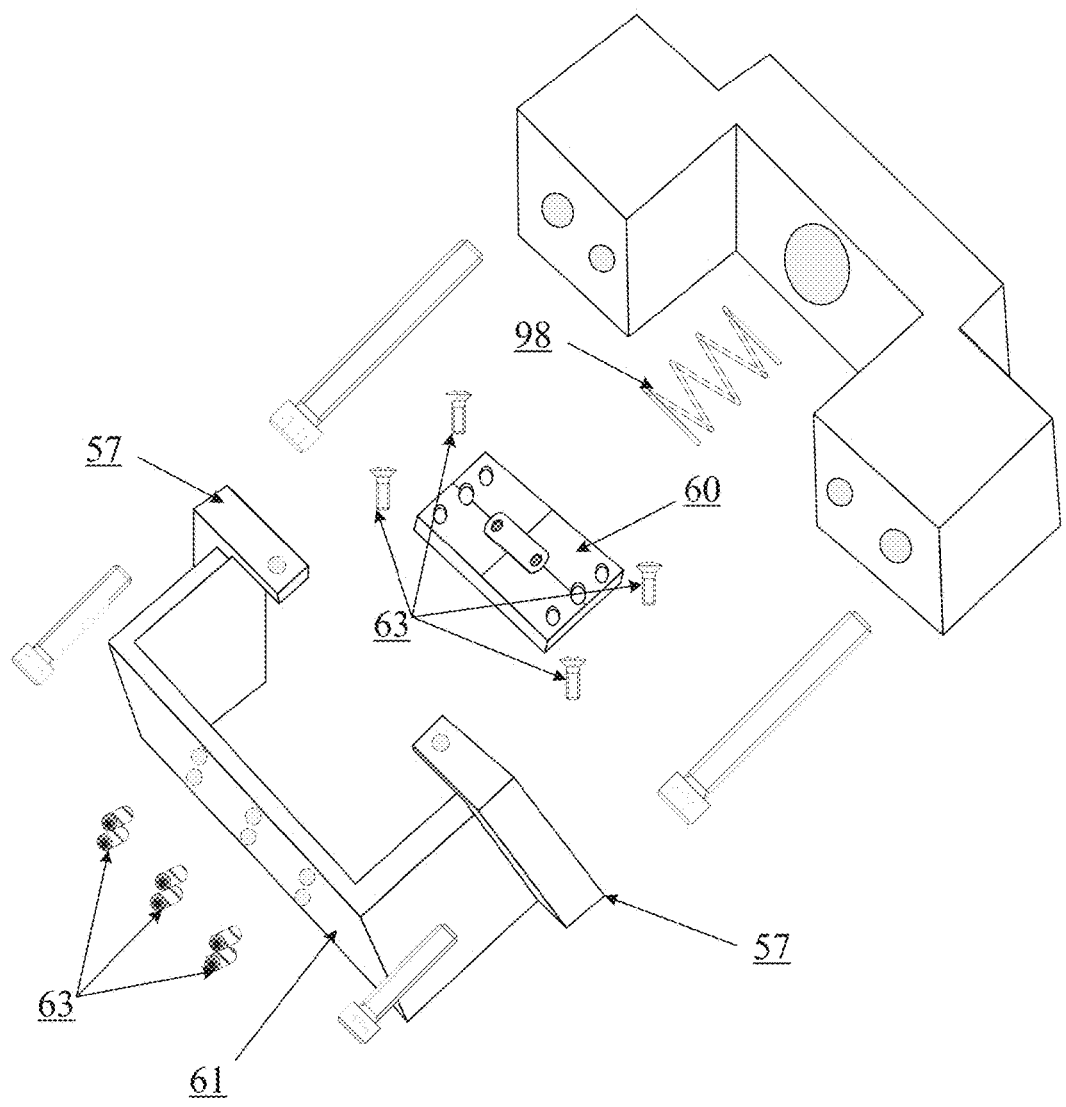
FIG. 4 is an exploded view of an embodiment of the adjustment assembly section of the fixture assembly of FIG. 3.

FIG. 4 provides an exploded view further illustrating components of the array affixing and adjusting assembly 54 of FIG. 3. The array-holding assembly 54 may be secured in a consistent and known position and orientation relative to the target assembly 56. Thus, depending on the shape and nature of the target assembly, various structures may be used to maintain the array-holder 54 in a known position relative to the target assembly. In the embodiment of FIGS. 3 and 4, the target assembly 56 may be secured to the array holder assembly 54 with rigid arms 58. Any other alternative structures may also be used.

Figure 5:
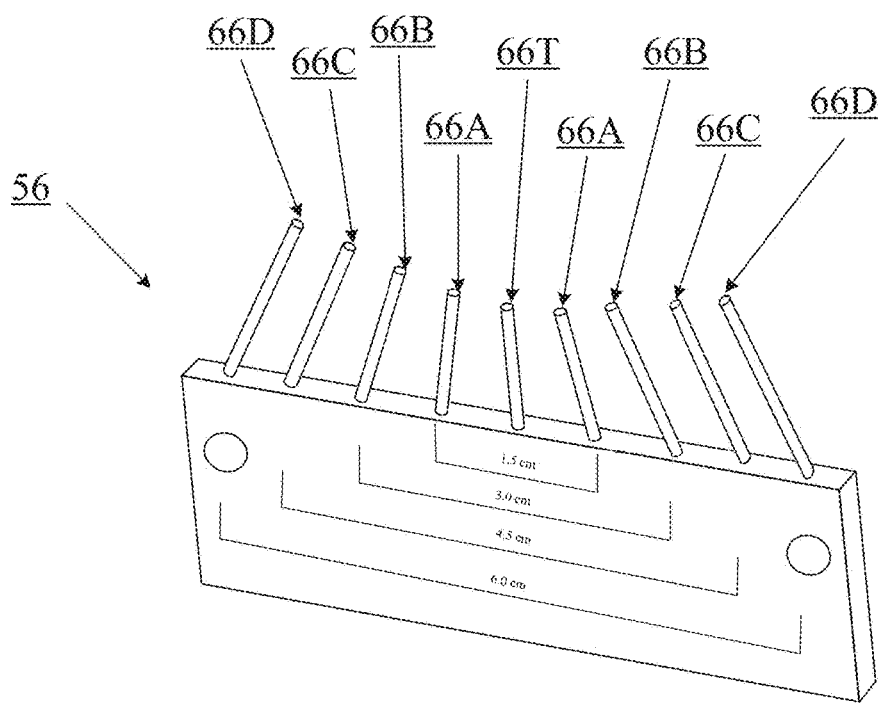
FIG. 5 is a perspective view of an embodiment of an alignment target made up of a plurality of pins.

FIG. 5 illustrates an embodiment of a target assembly 56 that may be used in an alignment process. In various embodiments, the target assembly 56 may include any structure with a known configuration of acoustic reflectors. A target 56 for use with an alignment process may generally have a pattern of reflectors that will allow for a clear indication of the array's alignment relative to the target 56. Targets ideal for an alignment process are those that include a plurality of reflectors (or holes) that lie in a precise known pattern in a single plane that may be precisely aligned with the intended imaging plane of the array. For example, the target assembly 56 shown in FIGS. 3-5 comprises a plurality of pins 66 (labeled as pins 66A-D and T in FIG. 5) arranged such that all of the pins 66 lie in a common plane that is coincident with the precisely aligned imaging plane.

As best seen in FIG. 5, the pins 66A-D and T may vary in length such that the tips of the pins may lie on multiple different points in the intended image plane (i.e., at different heights relative to a plane perpendicular to the imaging plane). In some embodiments, the pins may be oriented at angles such each pin's flat surface end may be oriented perpendicular to an arriving waveform transmitted from the array. In some embodiments, such angles may be selected assuming pings are transmitted from an origin at the center point of the array, even if pings are to be transmitted from multiple transmit elements at different locations on the array.

In some embodiments, target pins may be arranged in a common imaging plane and oriented at angles such that longitudinal axes of the pins intersect at a single point near the transducer array (e.g., above the transducer array's transmitting surface in some embodiments). For example, in some embodiments, pins furthest from a center pin (the end pins) may be oriented such that, with the target positioned at a minimum distance from the array, the end pins lie at a desired angle relative to the precision alignment element. For example, the end pins may be oriented at an angle of about 30 degrees relative to a line perpendicular to the precision alignment element in the imaging plane. Larger or smaller angles may be desirable depending on an angle of sensitivity of transducer elements in transducer arrays to be aligned.

When imaged by a transducer array to be aligned, each pin may appear as a dot. In this target configuration, each pin may appear as a dot in a known location on a display when the target is imaged by an aligned array supported in the array holder assembly.

In some embodiments, a target 56 may include a plurality of reflectors positioned so as to evaluate the array's alignment at various discrete distances from the target. For example, a target may include a center pin 66T and a plurality of pairs 66A-66D of pins laterally spaced equal distances from the center pin 66T. In various embodiments, a target may include any number of pairs of laterally-spaced pins. In some embodiments, the pairs of pins may be provided in a range of different lengths, meaning that some pairs of pins are closer to the transducer array than others. In various embodiments, alignment of an array may be evaluated at various distances from the target. In some embodiments, pin lengths may be calculated so as to place the faces of each pair of pins and the center pin 66T coincident with an arc of a transmitted wavefront at a selected depth.

In some embodiments, different reflectors of the target 56 may be configured and used for evaluating the array's alignment at different distances from the target 56 and/or for evaluating the array transmitting at different frequencies. For example, the target shown in FIG. 5 may include several pairs of reflectors of different lengths to be imaged at different vertical distances between the array and the target. As shown, the first pair of reflectors 66A may be configured for evaluating an array's alignment at a target-distance of about 1.5 cm, the second pair 66B of reflectors may be configured for evaluating an array's alignment at a target-distance of about 3.0 cm, the third pair 66C may be configured for evaluating an array's alignment at a target-distance of about 4.5 cm, and the fifth pair 66D may be configured for evaluating an array's alignment at a target-distance of about 6.0 cm. In alternative embodiments, targets may be configured for testing an array at any distance as desired.

In further alternative embodiments, the target 56 may include phantom structures with reflectors made of any suitable ultrasonically-reflecting material in a variety of alternative configurations. For example, the target may comprise a plurality of small sphere-shaped reflectors embedded in a solid material. Generally, a target may include any number of reflectors made of an appropriate echogenic material, as determined by the frequency and array style, that provides a small reflective surface relative to the wave length of the sound being used. Such reflective objects may be encased in precisely known locations in a sonolucent material. The sonolucent material to be used may be selected to be similar to conditions to be experienced by the array in an intended application. As such, in some cases, a sonolucent material may or may not offer attenuation. Reflectors in a target assembly need not be arranged in a symmetrical pattern, but preferably include multiple points at multiple different known locations such that alignment may be evaluated. The target may generally include any pattern of reflectors which may be supported within a solid, liquid or gaseous medium (depending on the intended use application). In some embodiments, a target may also include one or more "holes"—regions or objects that substantially absorb and do not reflect significant ultrasound signals. In some embodiments it may be desirable for reflectors or holes to be aligned in a single plane that is may be aligned with the ideal imaging plane.

In some alternative embodiments, a target may include any substantially static object that may be imaged with an ultrasound probe. For example, any number of phantoms designed for sonographer training are widely commercially available from various suppliers of medical equipment. Some commercially available phantoms are made to mimic the imaging characteristics of objects to be imaged such as specific or generic human tissues. Such properties may or may not be used in combination with various embodiments described herein. An object need not be purpose-built as a phantom to be used as a phantom for the alignment processes described herein.

Figure 6:
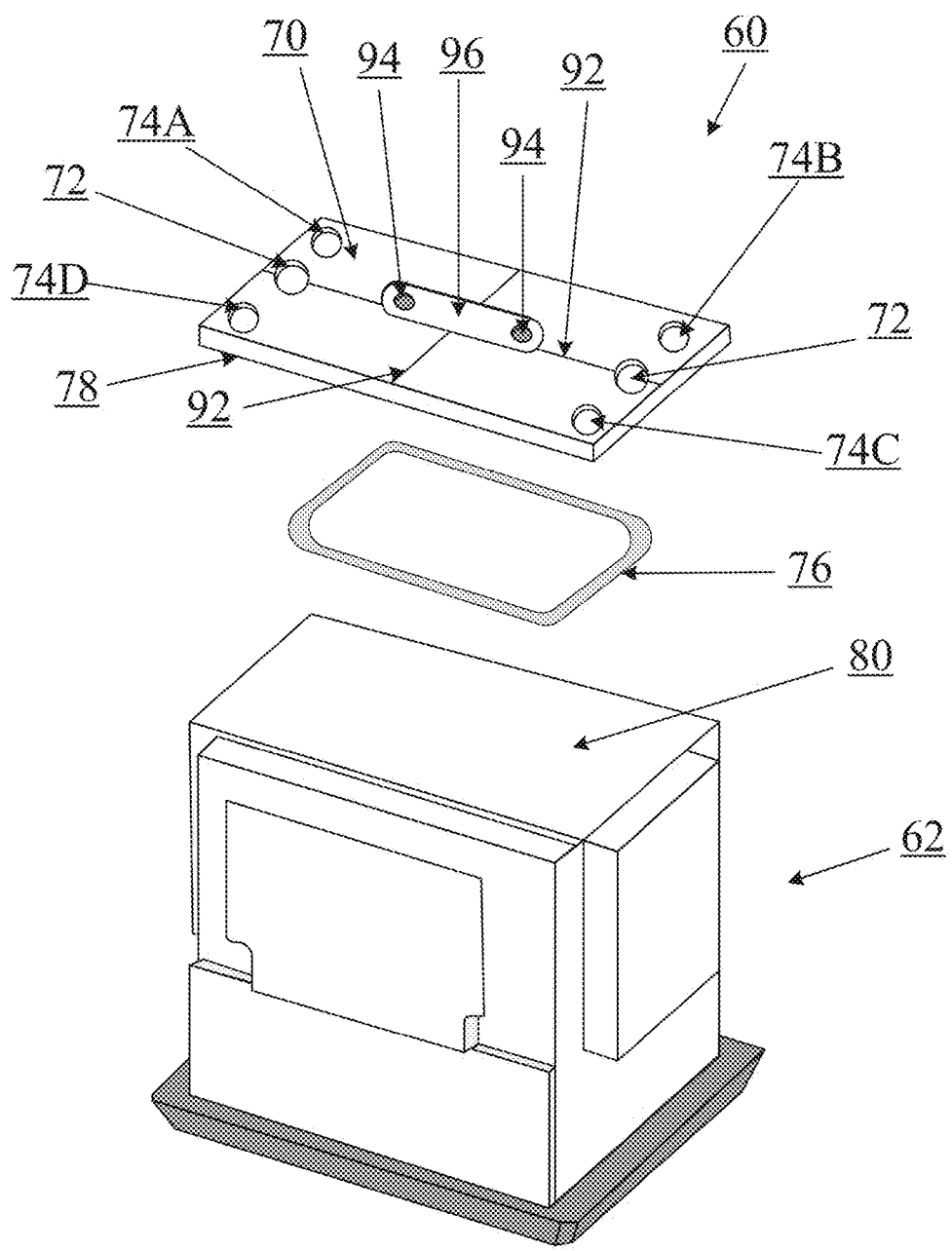
FIG. 6 is an exploded view of an embodiment of a transducer array, a gasket element, and a precision alignment element.

As shown in FIG. 6, in some embodiments, the PAE 60 may include a plate 70 with precisely positioned mounting holes 72 precisely arranged for attachment to the holder 54. For example, in some embodiments the PAE 60 may include two alignment mounting holes 72 configured to mount the PAE 60 to mounting arms 57 of the adjustment assembly (shown in FIGS. 3 and 4). The PAE 60 may further include corner holes 74A-74D for receiving set screws and for mounting the PAE 60 to a probe alignment bracket in a final probe assembly (e.g., as described below with reference to FIG. 12). In some embodiments, temporary set screws in the corner holes 74A-74D may also be used to adjust the position of an array relative to the PAE during an alignment procedure as described in further detail below. In some embodiments, the corner holes 74A-74D may be tapped with fine pitch threads.

In alternative embodiments, a precision alignment element may be provided in a variety of different structures, and may include any suitable features to ensure and/or to verify accurate and precise positioning of the PAE 60 relative to the target 56. For example, the PAE may include holes, pins, recesses or other structures configured to engage (or to be engaged by) corresponding structures on a holder assembly. In general, a precision alignment element (or PAE) may be any structure that may be mounted in a known precise position relative to a target in an alignment test assembly. Similarly, alternative holder assembly structures may include clamps, screws, pins, holes, recesses and various other mechanical structures configured to engage corresponding portions of a PAE and to hold a PAE in a consistent known position and orientation relative to a target.

In some embodiments, precision alignment features may be integrated into a probe alignment bracket (such as that described below with reference to FIG. 12. In such embodiments, a probe alignment bracket configured to support transducer arrays in a desired orientation relative to one another may include array-mounting sections, gasket-supporting sections and holes for injecting a flowable solidifying material once an array is aligned. In such some embodiments, a plurality of targets may be provided such that each array has a corresponding target arranged perpendicular to the aligned array plane. Alternatively, a target or a PAE holder may be adjustable so as to position the bracket PAE and the target(s) in a perpendicular orientation.

FIG. 6 illustrates an embodiment of a PAE 60 and a gasket 76 for adjustably securing the PAE 60 to a transducer array 62. In some embodiments, the PAE 60 may comprise a plate with a lower surface 78 sized and configured to be bonded to a back surface 80 of a transducer array.

Figure 7:
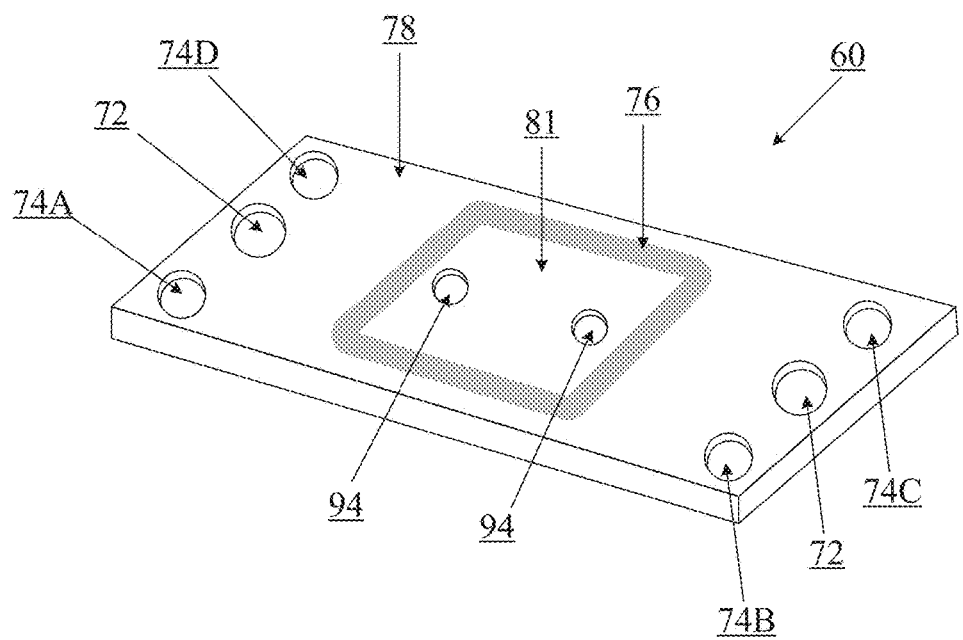
FIG. 7 is a perspective view of an embodiment of the lower side of the precision alignment element of FIG. 6.

As shown in FIG. 7, in some embodiments the lower surface 78 of the PAE 60 may include a recessed section 81. The recessed section 81 may be machined (or otherwise formed) to a precise depth and dimensions for creating a gasket 76. In some embodiments, a gasket 76 may be formed by extruding a bead or injecting a flow of a liquid or flowable solidifying material (e.g., RTV silicone, epoxy or other flowable solidifying material) around the perimeter of the recessed section 81 on the lower surface 78 of the PAE 60. In some embodiments, before the solidifying material cures, the PAE 60 and the gasket 76 may be pressed onto the back surface 81 of the transducer array 62.

Figure 8:
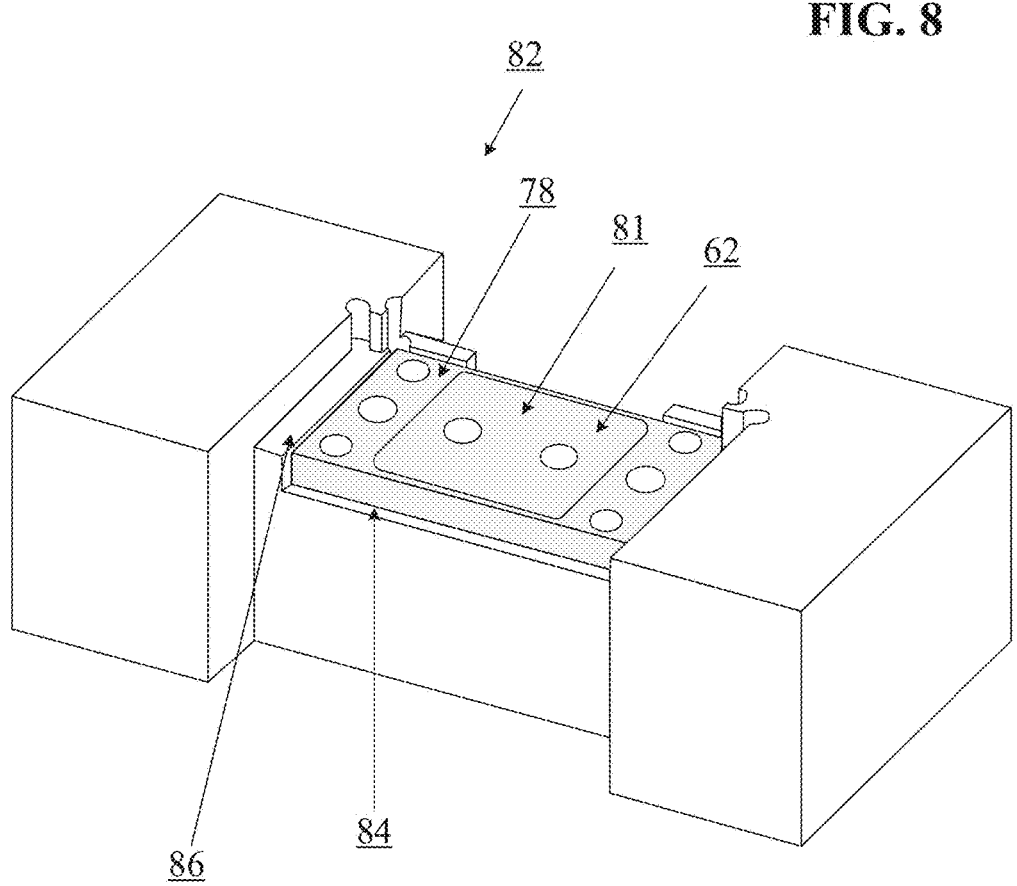
FIG. 8 is a perspective view of an embodiment of jig for establishing the thickness of the gasket of FIG. 6.

In some embodiments, a jig 82, such as that shown in FIG. 8, may be used to ensure that the gasket 76 is compressed to a consistent thickness. Using the jig 82, a consistent desired gasket thickness may be achieved by placing the PAE 62 in the provided slot 84, and then placing the transducer array 62 into the space above the PAE 62 until it abuts the shoulders 86 such that the height of the shoulders 86 above the PAE's lower surface 78 ensures a consistent spacing between the lower surface 78 of the PAE 60 and the back surface 80 of the transducer array 62.

It is generally desirable for the gasket to secure the PAE to the array while remaining somewhat flexible, allowing a small degree of movement between the PAE and the array during the alignment and adjustment process. Such flexibility may be achieved through selection of an appropriate flowable solidifying material and/or selecting a gasket thickness and width that allows sufficient flexibility. Alternatively, flexibility of the gasket may be achieved by performing the adjustment process before a hardening material completely cures.

In some embodiments, the PAE 60 and array 62 may be held within the jig 82 for a sufficient time for the gasket material to cure. Once cured, the PAE 62 will be temporarily secured to the back surface 80 of the transducer array 62 by the gasket, while allowing a small range of movement between the PAE 60 and the array 62. Although the use of a jig may provide a certain degree of precision to the assembly, the actual acoustic position of the transducer elements may not necessarily be precisely consistent with the physical back surface 80 of the transducer array 62 simply due to inevitable manufacturing variability.

In some embodiments, the PAE 60 may also include features and structures configured to facilitate precise alignment of the PAE 60 and an attached transducer array 62 with elements of a final probe assembly. For example, as shown in FIG. 6, the plate 70 may also include a plurality of holes 74A-74D precisely positioned for precisely mounting the alignment element 60 to a probe alignment bracket as will be described in further detail below with reference to FIG. 12. In some embodiments, the plate 70 may also include one or more channels 92 precisely sized oriented to engage corresponding structures in a probe alignment bracket.

In some embodiments, the PAE 60 may include one or more injection holes 94 through which a flowable solidifying material may be injected once the transducer array is determined to be perfectly aligned with the PAE (as will be described in further detail below with reference to FIG. 9). The PAE 60 may also include a relief 96 surrounding the injection holes 94 to prevent any overflowing affixing material from interfering with the fit of the PAE in a probe alignment bracket (as described in further detail below).

Figure 9:
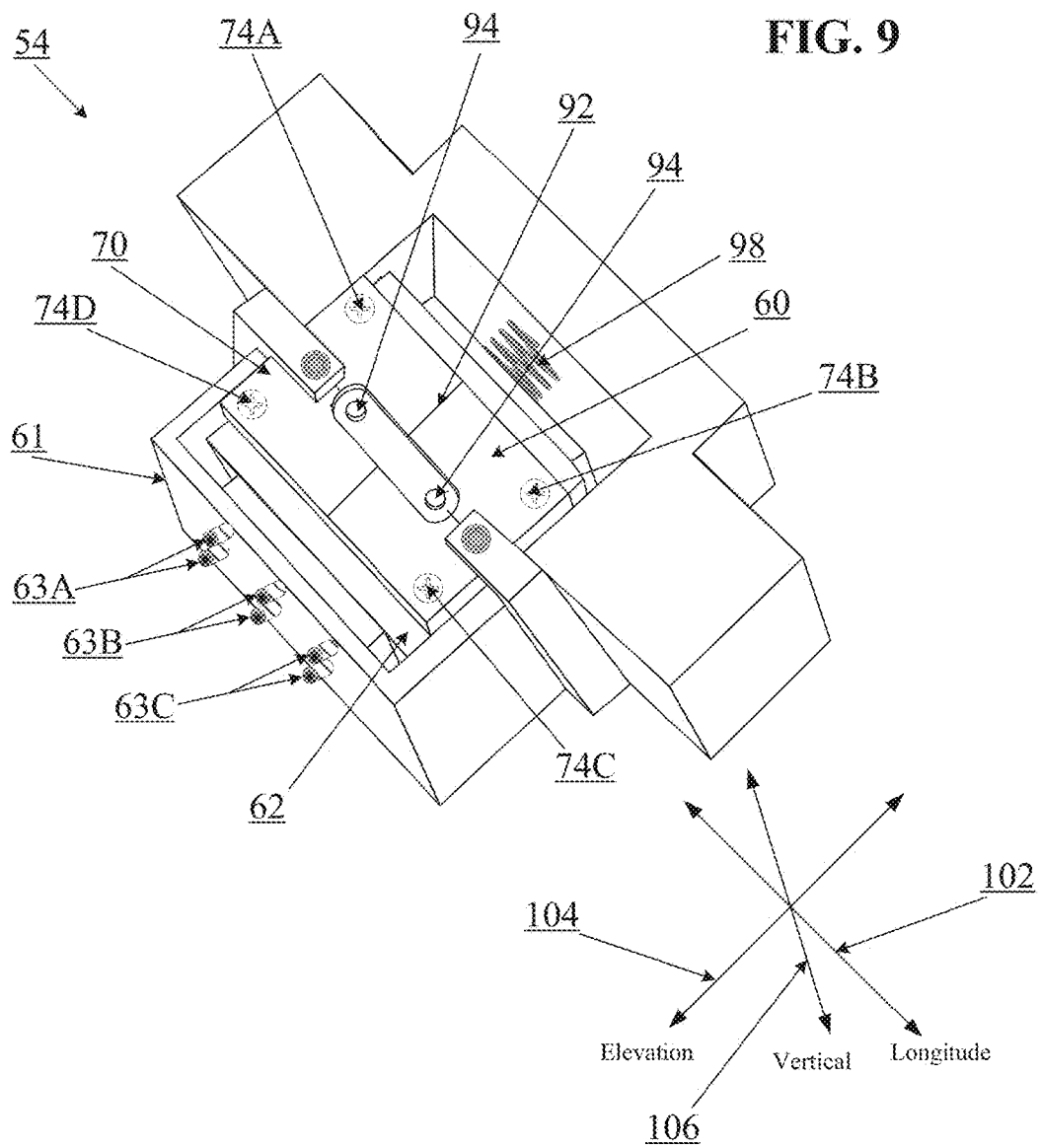
FIG. 9 is a perspective view of an embodiment of a transducer array mounted in an adjustment assembly.

FIG. 9 illustrates an array 62 to be aligned to a precision alignment element 60 and mounted in an adjustment assembly 54. The adjustment assembly 54 may generally include one or more adjustment mechanisms configured to move the array 62 relative to the PAE 60. In the illustrated embodiment, a plurality of set screws 63A-63C may be provided as adjustment mechanisms. A spring 98 (or other resilient material or device) may also be provided to mechanically bias the array towards the adjustment mechanisms so as to maintain contact between the array 62 and the set screws 63A-63C. In some embodiments, a point-contact device may be positioned between the spring 98 and the array 62. A point-contact device may be any structure that creates a small point of contact with the array, such as a pin, a nail, a sphere, a cone, or otherwise shaped structures. Any number of set screws in any desired arrangement may be used to adjust the position of the array 62 relative to the PAE 60.

FIG. 9 illustrates several set screws 63A-63C for adjusting the position of the array 62 relative to the PAE. The six adjustment set screws in the front surface of the adjustment cover 61 may be used for adjusting the position of the array by displacing a portion of the array in the Y direction. For example, tightening the bottom of the center screws 63B will tend to cause the array to pivot about the longitudinal axis 102, while tightening the right-side screws 63C or the left-side screws 63A will tend to cause the array 62 to pivot about the vertical axis 106. Tightening all of the front screws (or at least the top left and right side screws) may cause the array 62 to translate along the elevation axis 104. In some embodiments, adjustment set screws may also be used in one or more of the four corner holes 74A-74C in the PAE 60. Tightening a set screw in the screw right rear hole 74B will tend to cause the array to pivot about the longitudinal axis and the elevation axis. Thus, depending on the degree and the direction of misalignment detected during a testing step, one or more set screws may be adjusted until a desired adjustment of the array's position relative to the PAE 60 is achieved.

In various embodiments, ribbon connectors extending from the array may be electrically connected to a controller in order to transmit and/or receive ultrasonic signals using the transducer array. Any suitable connector may be used for achieving such electrical connections.

Alignment Imaging Controller Embodiments

Figure 10:
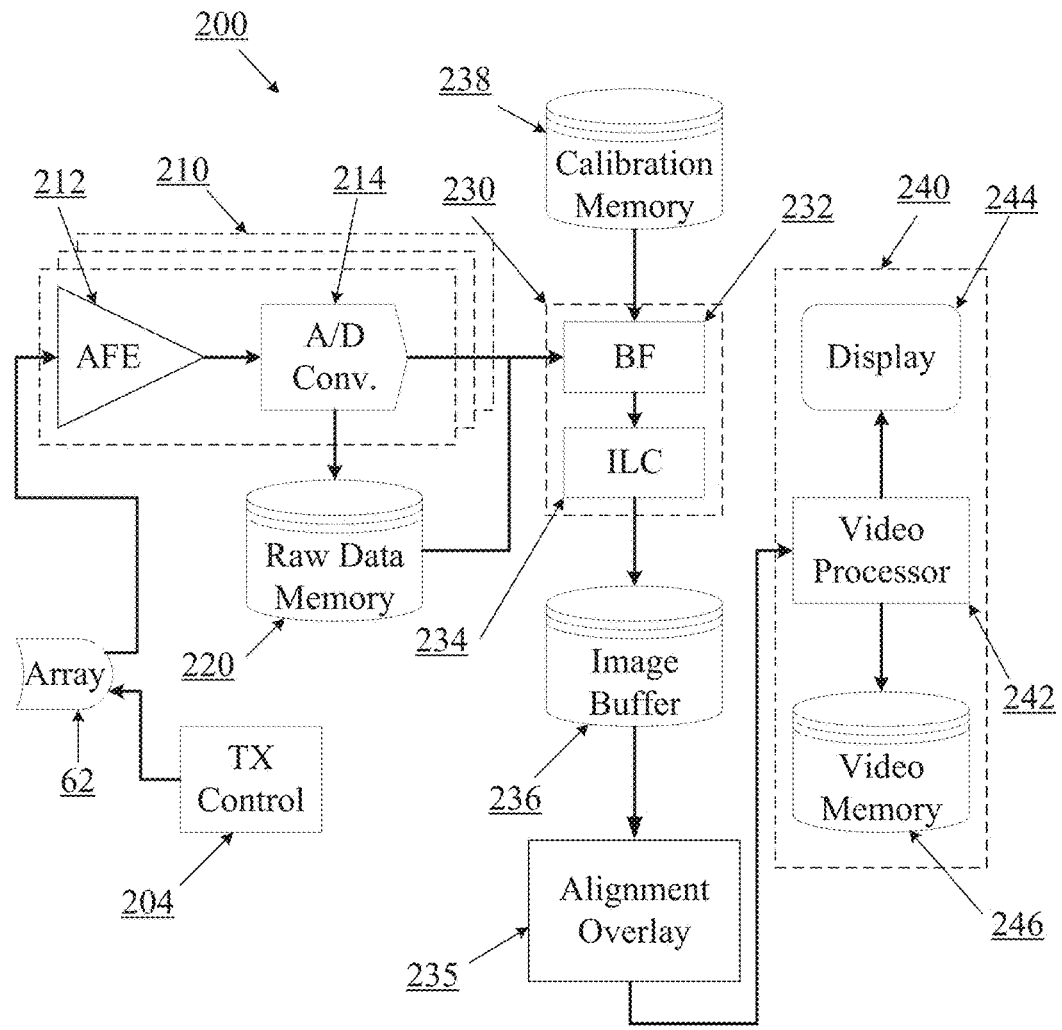
FIG. 10 is a block diagram illustrating an embodiment of an imaging controller for use with some embodiments of the alignment systems and methods herein.

FIG. 10 illustrates a block diagram of a controller 200 that may be used for controlling, transmitting, and receiving of ultrasound signals using the transducer array 62 during an alignment process. The controller 200 may also be configured to generate and display images based on the received echo data. In some embodiments, the controller 200 may further be configured to store raw echo data for later retrieval and analysis.

As shown in FIG. 10, a controller 200 may electronically and logically connected to a transducer array 202 to be aligned. In some embodiments, at least some of the transducer elements may be designated as transmit elements, while others may be designated as receive elements. In some embodiments, each transducer element may convert ultrasound vibrations into time-varying electrical signals and vice versa. In various embodiments, the array 62 to be aligned to a PAE may include any number of ultrasound transducer elements in any desired configuration.

The controller 200 may contain software and hardware elements configured to control an imaging process. In various embodiments of the alignment methods described herein, any imaging method (e.g., ping-based imaging, scanline-based imaging or any other available ultrasound imaging method) may be used for imaging the target assembly. Due to the use of transducer element position in ping-based beamforming methods, such methods may be particularly suited for an alignment evaluation process.

The transmission of ultrasound signals from elements of the array 62 may be controlled by a transmit controller 204. Upon receiving echoes of transmit signals, the transducer elements may generate time-varying electric signals corresponding to the received ultrasound vibrations. Signals representing the received echoes may be output from the array 62 and sent to a receive subsystem 210. In some embodiments, the receive subsystem may include multiple channels (e.g., one channel for each transducer element in some embodiments). Each channel may include an analog front-end device ("AFE") 212 and an analog-to-digital conversion device ("ADC") 214. In some embodiments, each channel of the receive subsystem 210 may also include digital filters and data conditioners (not shown) after the ADC 214. In some embodiments, analog filters prior to the ADC 214 may also be provided. In some embodiments, the output of each ADC 214 may be directed into a raw data memory device 220. Notably, the controller 200 need not include a scan converter for systems configured to use a ping-based imaging method.

In some embodiments, raw echo data may be stored in a raw data memory device 220 prior to any beamforming or image formation. In some embodiments, echo data may be passed directly from a receive subsystem 210 to an image formation sub-system 230.

The image formation sub-system 230 may include a beamformer 232 and an image layer combiner ("ILC") 234. If needed, image data may be temporarily stored in an image buffer memory device 236. In some embodiments, the image formation subsystem may retrieve stored echo data from the raw data memory device rather than receiving real-time echo data from the receive sub-system. The beamformer 232 may include or may have logical access to a memory device 238 containing transducer element position data. In the case of a new un-aligned and un-calibrated transducer array, such transducer element position data may be based on an idealized case for transducer arrays of a particular type. Alternatively, the transducer element position data may be based on calibration analysis of a plurality of previously-aligned arrays.

An alignment overlay subsystem 235 may include stored data including information describing known positions of reflectors in the target 56. In some embodiments, such an alignment overlay sub-system may include information for several targets which may be selectable by a user depending on which target is to be used. The alignment overlay subsystem may also include hardware and software for forming an image of expected reflector positions and additional information for assisting in assessing the alignment of a transducer array under examination.

The controller 200 may be further configured to output image data to a display sub-system 240. A display subsystem 240 may include a video processor 242 for performing various digital video image processing steps, a video memory 246 for storing "cine loop" data (e.g., processed video clips), and a display controller 244 configured to output image pixels to a display device.

Array Alignment Testing and Adjustment Method Embodiments

Thus, returning to the process diagram of FIG. 2, an embodiment of a process for aligning a transducer array 62 relative to a PAE 60 using an alignment apparatus such as that shown in FIGS. 3-6 will now be described. Once a PAE 60 has been temporarily mounted to an array 62 with a gasket 76, the PAE 60 and array 62 may be mounted in the adjustment section 54 of an alignment assembly 50. Ribbon connectors extending from the array 62 may then be electronically connected to an alignment imaging controller 200. In some embodiments, the degree of alignment (or misalignment) may then be tested by imaging the target assembly 56 with the array 62.

Because the position of the pin tips 66 may be known with a high degree of precision, the expected image produced by a perfectly-aligned array may be predicted with a high degree of precision. Thus, the actual obtained image may be compared with the theoretically ideal image, and the alignment of the array may be quantitatively and/or qualitatively evaluated. In some embodiments, such a qualitative comparison may be performed visually by a user. In order to assist in visually comparing the actual image with the theoretical image, a software layer may be configured to overlay a schematic representation of the theoretical image with the actual image. In some embodiments, the two images may be displayed in contrasting colors to further aid in distinguishing the actual image from the theoretical image.

FIGS. 11A and 11B illustrate an embodiment of an actual image of a target with five reflectors in precisely known positions. The reflector images are indicated by the amorphous-shaped patterns 110A-110E, and an overlaid theoretical image is indicated by the circles 112A-112E. FIG. 11A illustrates an example of an actual image that is misaligned with the target (and therefore, the array 62 is misaligned with the PAE 60, since the PAE 60 is known to be precisely aligned with the target). In some embodiments, a bar graph 114 (and/or a numerical value, a line graph or other quantitative visual information) may be displayed along with the theoretically correct image. Each bar of the bar graph 114 may indicate the intensity of reflectors lying within the ideal target region defined by one of the circles 112. Thus, each bar 115A-115E may correspond to each circle 110A-110E, which correspond to known positions of the reflectors (e.g., pins 66). A higher bar level may indicate better alignment of the actual image with the theoretical image for a given reflector position 110.

In the example of FIG. 11A, the center pin image 110C appears to be well-aligned while the images of the pins on the left 110A, 110B appear too high, and the image of the pins on the right 110D, 110E appear too low. This pattern may indicate that the array is misaligned in rotation about the elevation axis 104 (i.e., the left side of the array is too close to the target, and the right side of the array is too far away from the target), In view of this misalignment, the array 62 may be adjusted by tightening the right-side set screws 74B, 74C.

Misalignment due to rotation about the longitudinal axis 102 may be detected by recognizing that the images of all of the pins 110A-110C (or at least the center pin image 110C) is not as bright as expected. Such misalignment may be corrected by adjusting either the front screws 74D, 74C in the PAE or the rear PAE screws 74A, 74B depending on the suspected direction of misalignment about the longitudinal axis. In some cases, similar adjustments may be made my adjusting screws 63A-63C in the adjustment cover 61.

Misalignment about the vertical axis 106 may result in the images of pins further from the center being progressively less bright than the center pin image 110C. Such misalignment about the vertical axis may be corrected by tightening one or more of the adjustment screws 63A or 63C in the front plate 61 of the adjustment assembly 54.

In some embodiments, an assessment of the alignment of an array under test may be made based primarily on the imaged position of the center pin 110C and a single pair of pins equidistant from the center pin 110C. For example, the degree and direction of any misalignment of the array may be determined by evaluating the imaged position of only the center pin 110C and the two next-closest pins 110B and 110D relative to the expected positions of those pins.

FIG. 11B illustrates an example of an image that may be produced by an array that is substantially perfectly aligned with the target 56 and the PAE 60. In some embodiments, the degree of variation from the ideal image that may be allowable within a designed tolerance may be determined by experimentation.

In some embodiments, the step 26 (in the process of FIG. 2) of testing the alignment of an array 62 relative to a PAE 60 may be performed using a tank assembly such as that shown and described in U.S. patent application Ser. No. 12/760,327, now U.S. Pat. No. 8,473,239. In that system, the alignment of an array supported at an upper part of a tank may be tested by transmitting an ultrasound signal from the array and receiving echoes using a separate set of hydrophones located at the bottom of the tank.

With reference to FIGS. 6 and 9, once the array is found to be sufficiently aligned, the array 62 may be fixed in the new position relative to the PAE 60 by injecting a low viscosity flowable solidifying material through the injection holes 94 in the PAE. The solidifying material used in this step may have a sufficiently low viscosity to allow easy injection and filling of the space between the PAE and the array without altering the array's alignment relative to the PAE. The solidifying material may then be allowed to cure. In some embodiments, a quantity of flowable solidifying material may be injected into one hole 94 until the liquid solidifying material is seen extruding from the second hole 94. In other embodiments, a measured quantity of the flowable solidifying material approximately equal to the volume of the space between the PAE 60 and the back surface 80 of the array 62. Excess solidifying material may be allowed to extrude from the second hole. Once the solidifying material has cured, the array 62 will be secured to the PAE 60 in the aligned orientation, thus forming an aligned array-PAE assembly. At this point, the set screws may be removed or backed out from the adjusted positions, and the aligned array-PAE assembly may be removed from the adjustment and alignment assembly 54. If needed, the process may be restarted for a new array.

In various embodiments, some or all of the process of testing and adjusting alignment of a transducer array may be automated. For example, software may be provided and configured for evaluating misalignment of an array and selecting a suitable corrective adjustment as described above. Furthermore, robotic elements may be provided and configured to adjust the various set screws in order to automatically apply a corrective adjustment selected by a software agent. A robotic element may also be provided for injecting a quantity of a flowable solidifying material into the space between the PAE and the array.

Probe Assembly Method Embodiments

Figure 12:
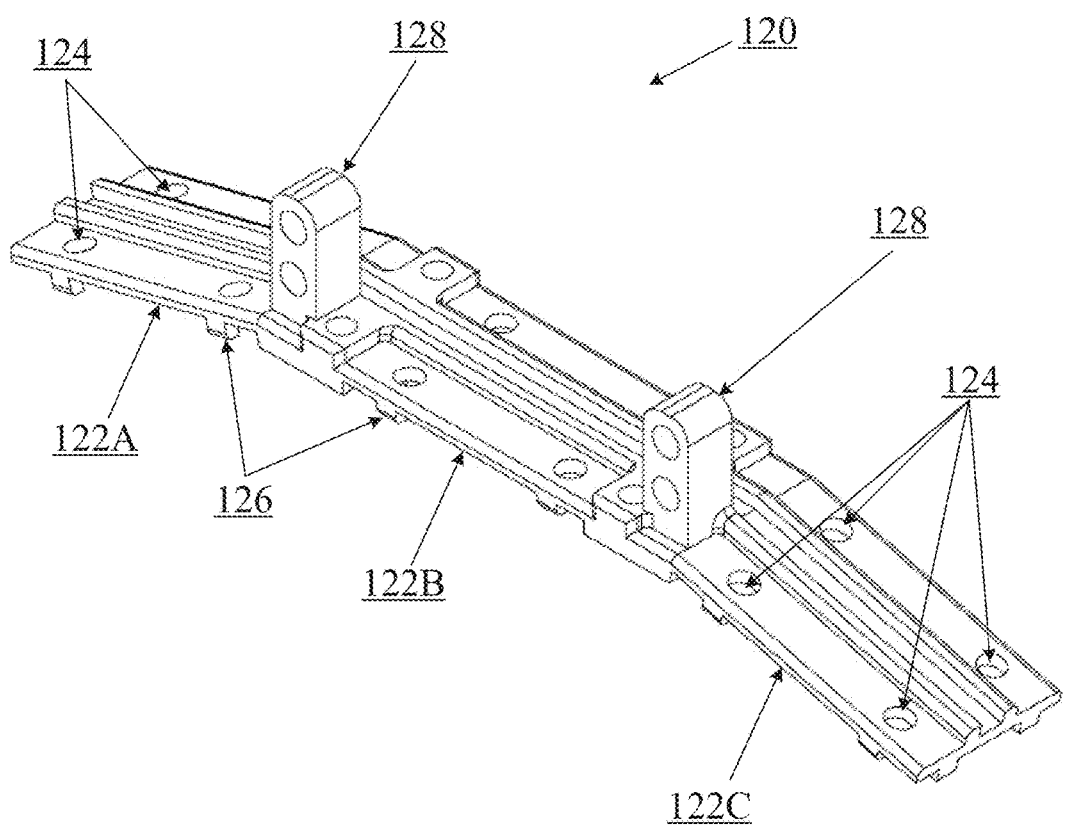
FIG. 12 is a perspective view of an embodiment of a probe alignment bracket for use in supporting transducer arrays in a designed orientation relative to a probe housing and relative to one another.
Figure 13:
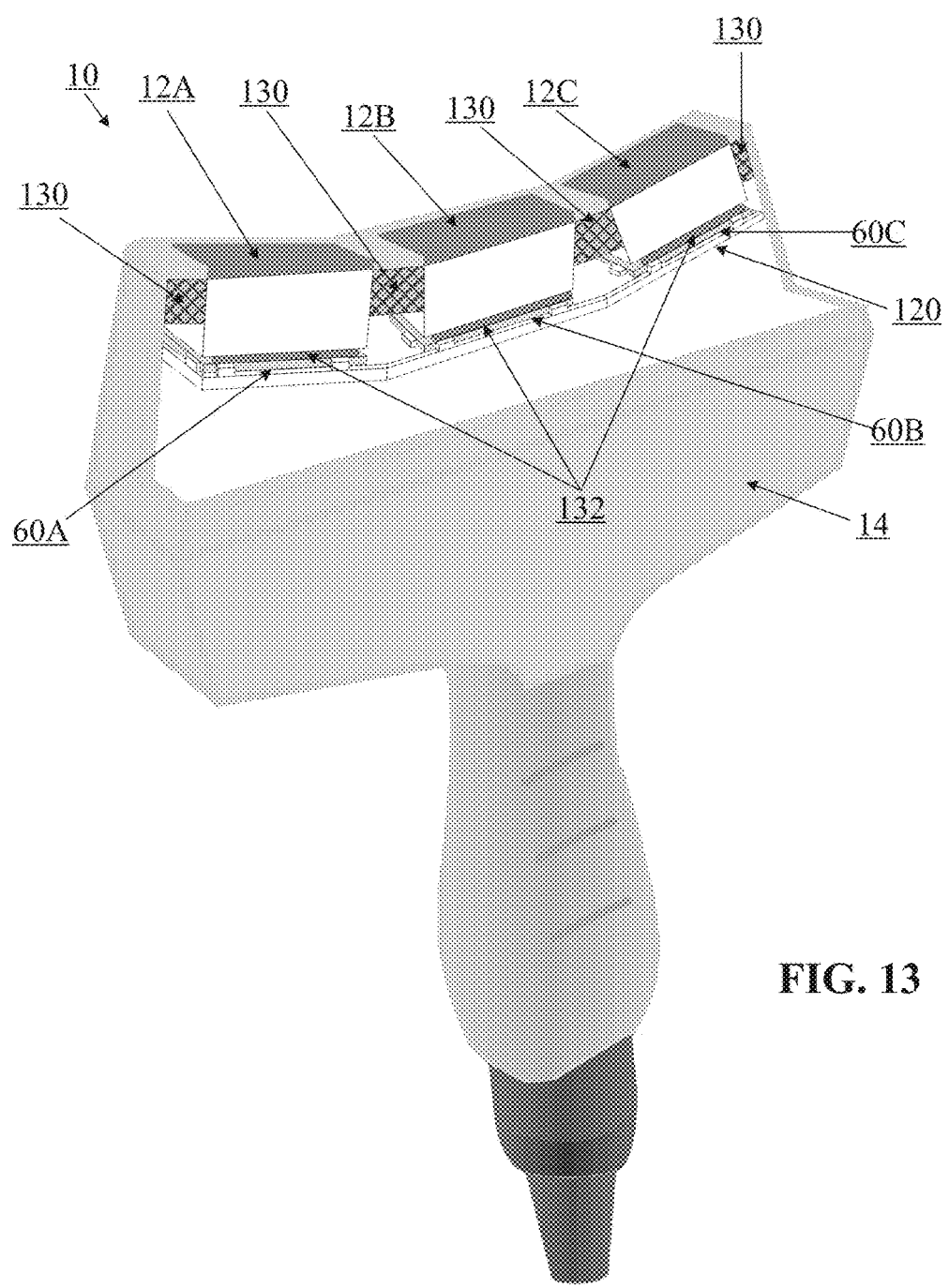
FIG. 13 is a cross-sectional view of an embodiment of a completed multiple aperture ultrasound probe assembled using the systems and methods described herein.

Once a sufficient number of arrays have been aligned to their respective PAEs, the aligned arrays may be mounted to a probe alignment bracket 120 such as that shown in FIG. 12 before final assembly into a probe housing 14 (FIG. 13). In some embodiments, a probe alignment bracket 120 may be provided with a plurality of array-receiving sections 122A-122C. Each array-receiving section 122A-122C may include structural features for receiving a PAE 60 attached to an aligned array 62. In some embodiments, the receiving sections 122A-122C may include ribs configured to engage channels 92 in the PAE 60 (FIG. 6). The receiving sections 122A-122C may also include a plurality of screw holes 124 through which mounting screws may pass for attaching PAEs 60 to the probe alignment bracket 120. The alignment bracket 120 may also include flanges 126 and/or other features to assist in positioning the PAEs in the proper positions. In other embodiments, a probe alignment bracket may have a wide range of shapes and configurations beyond that illustrated here depending on the number and designed orientation of arrays to be included in a probe.

In some embodiments, the probe alignment bracket 120 may also include attachment flanges 128 for securing an electronic connection board (not shown). An electronic connection board may be configured with a plurality of connectors configured for electrical connection to the flex connectors extending from each transducer array. In some embodiments, the connector board may further include traces connecting the transducer array connections to a common connector that may be configured for connection to a cable. Details of some embodiments of such connector boards and cabling assemblies may be seen in Applicants' U.S. patent application Ser. No. 13/272,098 titled "Multiple Aperture Probe Internal Apparatus and Cable Assemblies," which is incorporated herein by reference.

The probe internal assembly including the probe alignment bracket 120, connector board and aligned array-PAE assemblies may then be inserted into a probe housing 14 as shown in FIG. 13. In various embodiments, a probe housing 14 may include a one-piece construction, a clamshell construction, or any other suitable configuration. In some embodiments, portions of the internal assembly may be attached to portions of the probe housing by screws, bolts, clamps, clips, pins, or any other suitable attachment device.

Once the internal assembly is fully inserted into a probe housing 14, the aligned arrays 12A-12C and the probe alignment bracket 120 to which they are mounted may be permanently potted by injecting a flowable solidifying material 130 such as RTV silicone into the shell housing, surrounding at least portions of the arrays 12A-12C. In some embodiments, a flowable solidifying material 130 may also be injected further into the probe housing 14 so as to surround all or portions of the probe alignment bracket 12. In some embodiments, the flowable solidifying material may be used to substantially fill the space between the arrays and the sides of the probe housing 14. The solidifying material may also be smoothed out so as to provide a substantially consistent surface with the front surfaces of the arrays 12A-12C.

Embodiments of Completed Probe Assemblies

In various embodiments, a final probe assembled using the systems and methods described above may have some unique characteristics, some of which are illustrated in FIG. 13. As shown in the cross-sectional view of FIG. 13, a completed probe may include a plurality of transducer arrays 12A-12C potted into the probe housing 14 by a quantity of a solidified potting material 130 (e.g., RTV silicone or any other solidified flowable solidifying material). Each transducer array 12A-12C may be seen to be secured to a precision alignment element 60A-60C by an additional layer of a solidified material 132 between the precision alignment element 60 and the transducer array 12 (62). The layer of solidified material 132 may include the gasket (76 in FIGS. 6 and 7) and the affixing layer of solidifying material injected after aligning the array to the PAE. The precision alignment elements 60A-60C are, in turn, mounted to a probe alignment bracket 120 in precise positions.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A multiple aperture ultrasound probe comprising:
a probe housing;
a probe bracket positioned within and secured to the probe housing;
a first transducer array secured to a substantially planar plate-shaped first precision alignment element by a layer of a solidified polymer material interposed between a first surface of the first precision alignment element and a first surface of the first transducer array, a second surface of the first precision alignment element being secured to the probe bracket, wherein the first precision alignment element is a rectangular plate comprising a plurality of bracket-mounting holes adjacent corners of the rectangle and at least two alignment mounting holes located away from the corners;
a second transducer array secured to a substantially planar plate-shaped second precision alignment element by a layer of a solidified polymer material interposed between a first surface of the second precision alignment element and a first surface of the second transducer array, the second precision alignment element being secured to the probe bracket; and
a solidified polymer material disposed in a space between the probe bracket and the probe housing.

2. The probe of claim 1, wherein the first transducer array and the second transducer array are precisely aligned relative to the first precision alignment element and second precision alignment element, respectively.

3. The probe of claim 1, wherein the first precision alignment element comprises at least one hole through which a quantity of solidified polymer material extends.

4. The probe of claim 3, wherein the first precision alignment element comprises two holes, at least one of which has a quantity of solidified polymer material extending therethrough.

5. The probe of claim 1, wherein the first surface of first transducer array is approximately parallel to a surface defined by transducer elements.

6. The probe of claim 1, wherein only the first surface of the first transducer array is secured to only the first surface of the precision alignment element.

7. The probe of claim 1, wherein the first precision alignment element is secured to the probe bracket by a plurality of mechanical fasteners.

8. A multiple aperture ultrasound probe comprising:
a probe housing;
a probe bracket positioned within and secured to the probe housing;
a first transducer array secured to a substantially planar plate-shaped first precision alignment element by a layer of a solidified polymer material interposed between a first surface of the first precision alignment element and a first surface of the first transducer array, a second surface of the first precision alignment element being secured to the probe bracket;
a second transducer array secured to a substantially planar plate-shaped second precision alignment element by a layer of a solidified polymer material interposed between a first surface of the second precision alignment element and a first surface of the second transducer array, the second precision alignment element being secured to the probe bracket;
wherein the probe bracket comprises a rib engaging channels in the second surfaces of the first precision alignment element and second precision alignment element; and
a solidified polymer material disposed in a space between the probe bracket and the probe housing.

* * * * *